(12) United States Patent
Tarabichi

(10) Patent No.: US 7,455,647 B2
(45) Date of Patent: Nov. 25, 2008

(54) DYNAMIC SPACER FOR TOTAL KNEE ARTHROPLASTY

(76) Inventor: Samih Tarabichi, P.O. Box 32238, Dubai (AE)

( * ) Notice: Subject to any disclaimer, the term of this patent is extended or adjusted under 35 U.S.C. 154(b) by 186 days.

(21) Appl. No.: 10/626,407

(22) Filed: Jul. 24, 2003

(65) Prior Publication Data
US 2005/0020941 A1    Jan. 27, 2005

(51) Int. Cl.
*A61B 5/103* (2006.01)
*A61B 5/117* (2006.01)

(52) U.S. Cl. ................................. 600/587; 600/595

(58) Field of Classification Search ............. 600/595, 600/587; 433/72; 236/42; 606/90, 107; 408/10; 385/13; 439/131
See application file for complete search history.

(56) References Cited

U.S. PATENT DOCUMENTS

| | | | | | |
|---|---|---|---|---|---|
| 3,420,222 | A | * | 1/1969 | Noe et al. ................. 600/595 |
| 3,722,100 | A | * | 3/1973 | Weisman et al. ............. 433/72 |
| 4,171,768 | A | * | 10/1979 | Christiansson ............... 236/42 |
| 4,501,266 | A | * | 2/1985 | McDaniel ................... 606/90 |
| 4,687,384 | A | * | 8/1987 | McCoy ..................... 408/10 |
| 5,213,112 | A | * | 5/1993 | Niwa et al. ................ 600/587 |
| 5,484,447 | A | * | 1/1996 | Waldock et al. ............ 606/107 |
| 5,688,280 | A | | 11/1997 | Booth, Jr. et al. |
| 5,701,370 | A | * | 12/1997 | Muhs et al. .................. 385/13 |
| 5,800,438 | A | * | 9/1998 | Tuke et al. ................... 606/90 |
| 5,911,723 | A | | 6/1999 | Ashby et al. |
| 5,997,545 | A | | 12/1999 | Doherty et al. |
| 6,361,506 | B1 | * | 3/2002 | Saenger et al. ............. 600/587 |
| 6,716,043 | B2 | * | 4/2004 | Ishizuka ................... 439/131 |
| 2004/0260208 | A1 | * | 12/2004 | Laprade et al. ............. 600/595 |

OTHER PUBLICATIONS

M.J. Winemaker, M.D., Fresc©, Perfect Balance in Total Knee Arthroplasty, The Journal of Arthroplasty vol. 17 No. 1 2002.

* cited by examiner

*Primary Examiner*—Max Hindenburg
*Assistant Examiner*—Jeffrey G Hoekstra
(74) *Attorney, Agent, or Firm*—Warner J. Delaune; Baker Donelson, et al.

(57) ABSTRACT

A dynamic spacer is provided for measuring flexion-extension gap during total knee arthroplasty. The dynamic spacer includes a first planar member having a lower tissue engaging surface, and a second planar member having an upper tissue engaging surface. A tensioner is disposed between the first planar member and the second planar member for applying a tensile force acting upon the first and second planar members. The tensioner is attached to the first and second planar members, such that the first planar member is held substantially parallel to the second planar member in the absence of compressive load. The dynamic spacer allows for accurately measuring flexion-extension gaps and angular deviation in flexion indicating the appropriateness of femoral rotation.

8 Claims, 3 Drawing Sheets

DYNAMIC SPACER FOR TOTAL KNEE ARTHROPLASTY

STATEMENT REGARDING FEDERALLY SPONSORED RESEARCH OR DEVELOPMENT

Not Applicable

FIELD OF THE INVENTION

The present invention relates to a surgical instrumentation system used during total knee arthroplasty.

BACKGROUND OF THE INVENTION

Surgical techniques for total knee arthroscopy ("TKA") involve the measurement of the flexion and extension gaps. Soft tissue imbalance and bony misalignment can lead to malfunction and failure, thus the accurate measurement of the flexion and extension gaps is critical to a successful TKA procedure.

Surgical techniques for TKA typically begin with resection of the proximal tibia, and the balancing of the soft tissues of the knee in extension. The knee is then placed into flexion and a cutting block employed to obtain a rectangular flexion gap while the knee is distracted in flexion. After measuring the flexion gap, the distal femur is then resected. The knee is placed back into extension and the extension gap is measured and compared to the flexion gap. Additional resection of the distal femur is performed if required to ensure equal gaps.

The flexion and extension gaps should be as nearly equal as possible when the collateral ligaments are taut. Such tensioning is necessary because tendons and ligaments are relatively inextensible, and the spatial differences between the prosthetic knee and the natural joint may result in excessive tensile forces or excessive looseness. Tensioning the soft tissue while balancing flexion and extension gaps ensures stability and a full range of motion. If an implant is selected to fit the flexion gap and the flexion gap exceeds the extension gap, the knee will be incapable of full extension. Conversely, if the extension gap exceeds the flexion gap, the knee will hyper-extend and will be unstable in full extension. If an implant is selected to fit the extension gap, similar problems arise in flexion, as does the risk of dislocation There are basically three existing surgical instrumentation systems for measuring flexion-extension gap. The first system employs solid blocks of different thickness called spacers. After making the preliminary bone cuts, a spacer of known thickness is inserted into the knee during flexion and extension. The surgeon typically distracts the knee and observes the soft tissues around the block to ensure they are balanced. If either the tension in the soft tissues or the flexion-extension gap is not balanced, then additional bone resection may be required. This system does not measure the tension in the soft tissue, but instead relies on the subjective perception of the surgeon and his ability to reliably and repeatedly distract the knee in flexion and in extension.

The second system employs a pair of distraction clamps, which are similar to large pliers. One clamp is used to distract the medial soft tissue while the other is used to distract the lateral soft tissue. With the soft tissue distracted, the flexion and extension gaps are measured either by additional instrumentation or with the distraction clamps if they provide means for measuring distances between bone surfaces. Distraction clamps are often quite large, particularly if they also perform measurement functions, and clamps have the tendency to damage the bone surfaces in which they make contact. Also, the surgeon must tension the clamps manually and ensure equal tension across the lateral-medial plane, which often proves to be a difficult process.

The third system employs a device known as a tensor designed to tense the knee during flexion and extension. After resection of the proximal tibia and the posterior femoral condyles and with the knee in flexion, the surgeon inserts the tensor into the flexion gap. The surgeon then operates the device by turning knobs or squeezing handles, which tensions the collateral ligaments. After applying a predetermined force, the device may be used to measure the flexion gap. The process is repeated with the knee in extension. The measured flexion gap is used as a guide to mark the distal femur at a location where the bone may be resected to provide an extension gap as near as possible to the measured flexion gap. The conventional tensor is not very practical due to the device's complexity and due to difficulties associated with its use.

SUMMARY OF THE INVENTION

Given the disadvantages of conventional surgical instrumentation systems for measuring flexion-extension gap, the present invention, a dynamic spacer, provides an improved instrumentation system that it easy to use, simple in construction, and accurately measures flexion-extension gaps under repeatable soft tissue tension.

Unlike conventional spacers, the dynamic spacer applies tension to the soft tissue without relying on the surgeon to repeatedly and accurately distract the knee in flexion and extension. Also, the dynamic spacer does not require removal prior to extension of the knee, thus instead of serving as a guide for distal femur resection, the dynamic spacer accurately measures the difference between the flexion and extension gaps and minimizes the possibility that successive distal femoral cuts will be required to increase the extension gap or the possibility that the distal femoral surface will require packing with bone cement if the extension gap is too large.

Furthermore, the dynamic spacer can also indicate whether rotation of the distal femur is appropriate. Significant angular deviation of the dynamic spacer in flexion indicating a trapezoidal flexion gap may be corrected by adding external femoral rotation when making the posterior femoral cut. The external rotation improves patellar tracking and minimizes posteromedial wear of the femoral component of the prosthetic knee, particularly in a degenerative valgus knee. Surgeons employing conventional spacers must rely on their subjective observation to determine the appropriateness of femoral rotation. However, accurate measurements of deviations from rectangular flexion gap can be determined when employing the dynamic spacer of the present invention.

The dynamic spacer of the present invention provides a surgical tool for measuring the flexion and extension gaps located between the previously resected surfaces of the proximal tibia and the distal femoral condyles during TKA. The dynamic spacer generally comprises a first planar member having a lower tissue engaging surface, a second planar member having an upper tissue engaging surface, and a tensioning means disposed between the first planar member and the second planar member for applying a tensile force acting upon the first and second planar members. The tensioning means is fixedly attached to the first and second planar members, such that the first planar member is held substantially parallel to the second planar member in the absence of compressive load. The dynamic spacer of the present invention also includes a means for measuring the distance between the lower tissue engaging surface of the first planar member and the upper tissue engaging surface of the second planar member and a means for measuring the angulation of the second planar member as the second planar member deviates from parallel with respect to the first planar member.

PREFERRED EMBODIMENTS OF THE INVENTION

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figure 1:
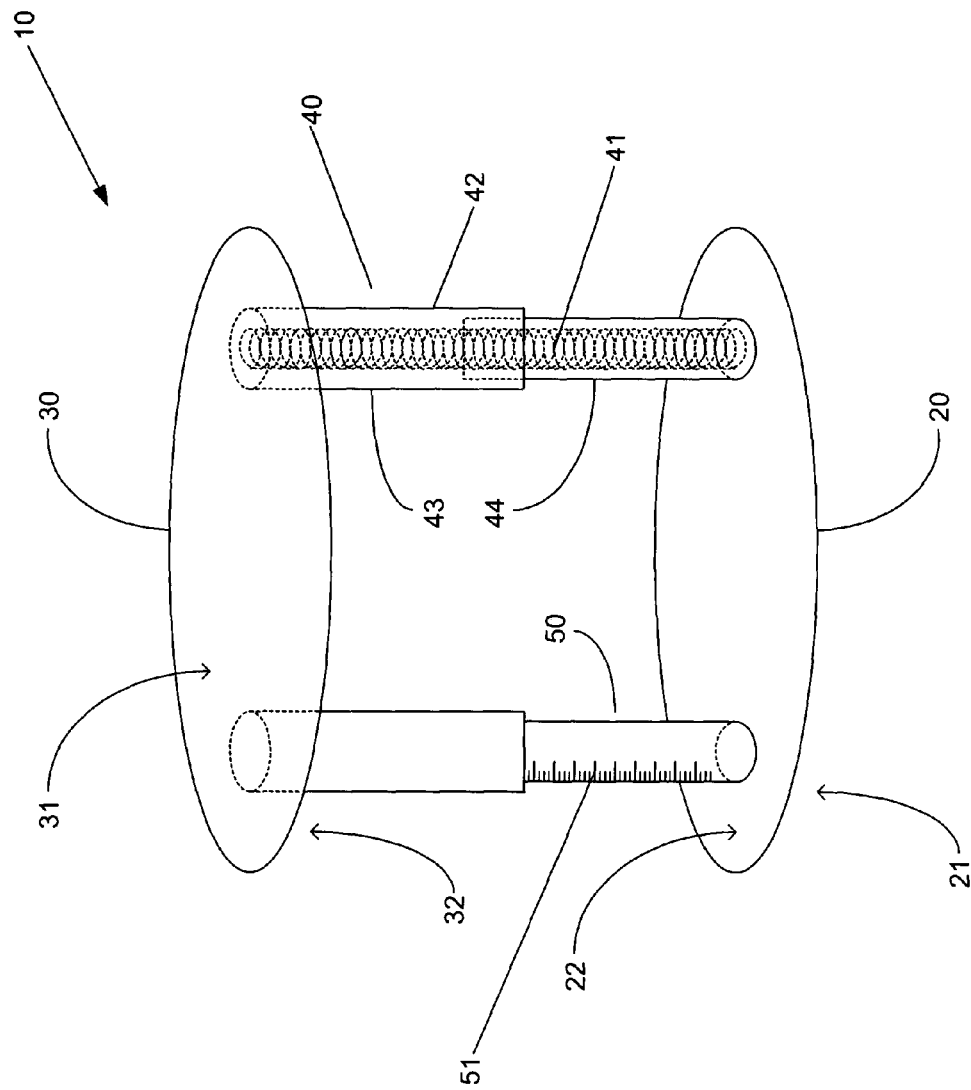
FIG. 1 is a front-side perspective view of one preferred embodiment of the dynamic spacer of the present invention featuring a plurality of compressive coil type springs, wherein a segmental spring housing surrounds each spring.

FIG. 1 illustrates one preferred embodiment of the present invention. The dynamic spacer 10 comprises a first planar member 20 having a lower tissue engaging surface 21 and an upper tensioning surface 22 and a second planar member 30 having an upper tissue engaging surface 31 and a lower tensioning surface 32. The shape of the first and second planar members 20, 30 is substantially oval, however, any suitable shape that can be inserted into the surgically prepared knee capsule may be employed. The first and second planar members 20,30 may be constructed of any suitable material, but is preferably stainless steel or similar biocompatible metal alloy. A tensioning means 40 is sandwiched between the first and second planar members 20, 30 and is fixedly attached to the upper tensioning surface 22 of the first planar member 20 and the lower tensioning surface 32 of the second planar member 30 such that the second planar member 30 is substantially parallel to the first planar member 20 in the absence of any compressive load on the tensioning means 40. The tensioning means 40 employed in the present invention may be any device that applies tensile force, including compressive coil type springs, torsion springs, and pneumatic devices, such as air springs or pneumatic cylinders. In the one preferred embodiment illustrated in FIG. 1, the tensioning means 40 comprises a plurality of compressive coil type springs 41, wherein each spring 41 is surrounded by a segmental spring housing 42.

Figure 2:
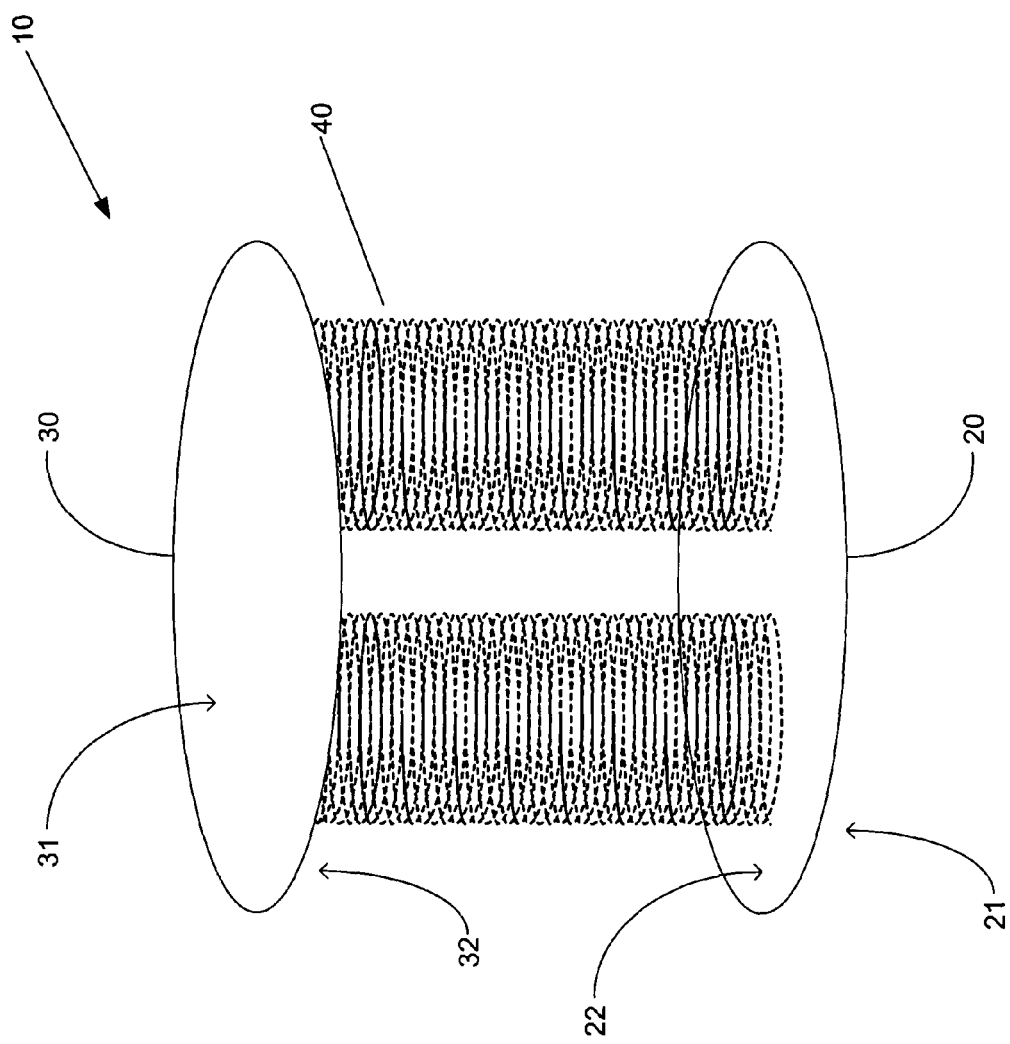
FIG. 2 is a front-side perspective view of another preferred embodiment of the dynamic spacer of the present invention featuring a plurality of compressive coil type springs.
Figure 3:
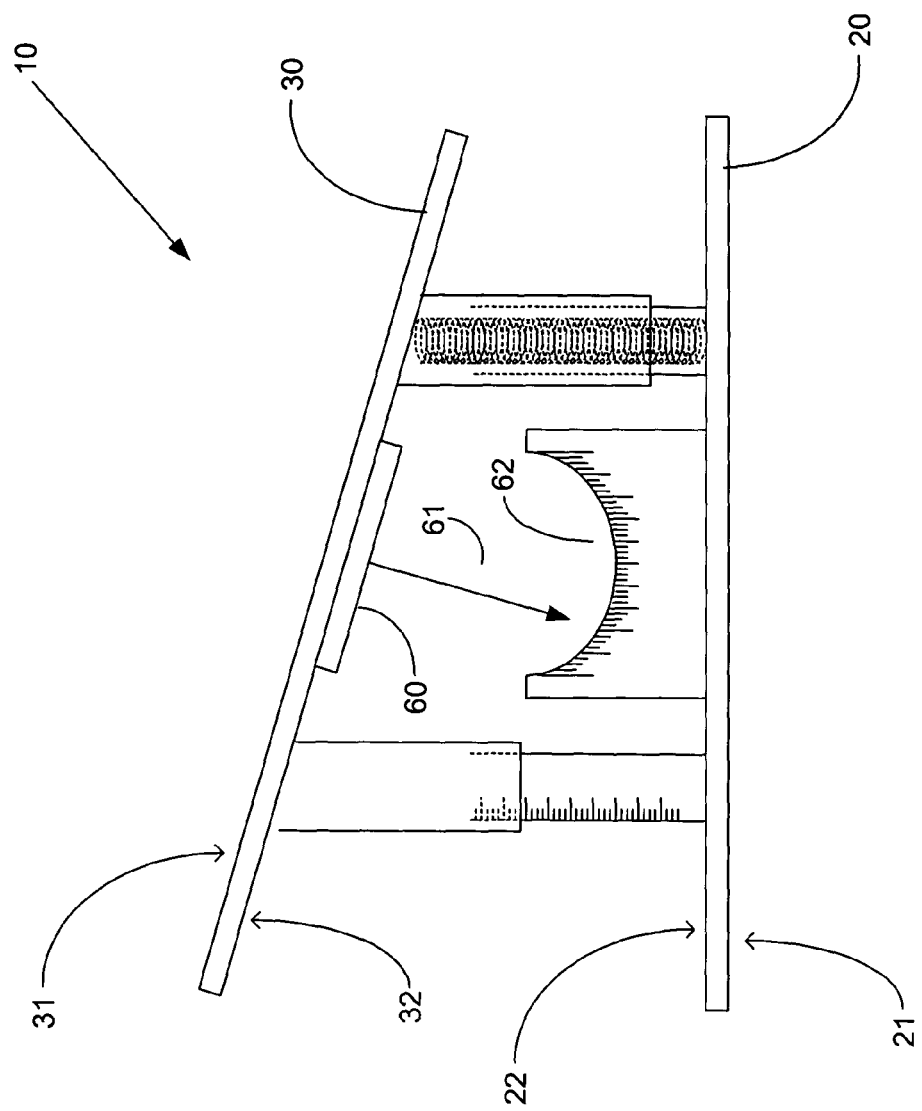
FIG. 3 is a front-side perspective view of one preferred embodiment of the dynamic spacer of the present invention under compressive load and featuring a means for measuring the angulation of the second planar member.

FIG. 2 shows another preferred embodiment of the present invention. In this embodiment, the tensioning means 40 comprises a plurality of compressive coil type springs that are not surrounded by any type of housing.

Considering the tensioning means 40 of FIG. 1 in more detail, the spring housing 42 surrounding the spring 41 comprises an upper housing section 43 and a lower housing section 44. The upper and lower housing sections 43, 44 may have any desired shape, but the preferred shape shown in FIG. 1 is cylindrical. The lower cylindrical housing section 44 is fixedly attached to the tensioning surface 22 of the first planar member 20 and the upper cylindrical housing section 43 is fixedly attached to the tensioning surface 32 of the second planar member 30. The diameter of the upper cylindrical housing section 43 is slightly larger than that of the lower cylindrical housing section 44, which allows the upper cylindrical housing section 43 to slidingly engage the exterior surface of the lower cylindrical housing section 44. With the spring housing 42 attached to the first and second planar members 20, 30, it is not necessary for the compressive spring 41 to be fixedly attached to any portion of the dynamic spacer 10. This allows for easy replacement of worn springs 41 and allows the disassembly of the dynamic spacer 10 for proper sterilization.

The dynamic spacer of the present invention includes a means for measuring the distance between the lower tissue engaging surface 21 of the first planar member 20 and the upper tissue engaging surface 31 of the second planar member 30. A preferred embodiment of the means for measuring this distance is shown in FIG. 1. The lower cylindrical housing section 44 of spring housing 42 comprises graduated markings 51 on its exterior surface 50. As the upper cylindrical housing section 43 moves along the exterior surface 50 of the lower cylindrical housing section 44, the graduated markings 51 reveal the distance between the lower tissue engaging surface 21 of the first planar member 20 and the upper tissue engaging surface 31 of the second planar member 30.

If each spring housing 42 comprises graduated markings 51, the difference in the measured distances for each spring housing 42 may be used to determine the angulation of the second planar member 30 as the second planar member 30 deviates from parallel with respect to the first planar member 20. As shown in FIG. 2, a simpler, alternative means for deriving the angulation of the second planar member 30 may be employed.

The second planar member 30 may include a bracket 60 that is secured to the lower tensioning surface 32. A positioning needle 61 is secured to the bracket 60 and extends downward and perpendicular to the lower tensioning surface 32. Alternatively, bracket 60 and positioning needle 61 may be integrally formed as a single component. Oppositely disposed and secured along the upper tensioning surface 22 of the first planar member 20 is an angulation gauge 62. As the second planar member 30 deviates from parallel with respect to the first planar member 20, the positioning needle 61 varies its position relative to angulation gauge 62. Graduated markings 63 on angulation gauge 62 may be used to measure the second planar member 30 deviations.

While the dynamic spacer 10 disclosed herein has been disclosed as a simple mechanical device, the mechanical means for measuring the distance between the tissue engaging surfaces 21, 31 and the angulation of the second planar member 30 could easily be performed by conventional optomicroelectronic means. In addition, other electronic measurements, such as tension gauges, may be incorporated into the device. By employing electronic measurement means, continuous measurements can be taken and digitally displayed and recorded.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A dynamic spacer for measuring flexion and extension gaps during knee arthroplasty, the dynamic spacer comprising: a first planar member having a lower tissue engaging surface and an upper tensioning surface, a second planar member having an upper tissue engaging surface and a lower tensioning surface, and a tensioning means residing entirely between said upper tissue engaging surface and said lower tissue engaging surface for applying a tensile force acting upon said first and said second planar members during the measuring of the flexion and extension gaps, said tensioning means fixedly attached to said upper tensioning surface of said first planar member and said lower tensioning surface of said second planar member, wherein said dynamic spacer is configured to reside completely internally to the knee during said knee arthroplasty.

2. The dynamic spacer of claim 1, further comprising a means for measuring a distance between said lower tissue engaging surface of said first planar member and said upper tissue engaging surface of said second planar member.

3. The dynamic spacer of claim 2, further comprising a means for measuring an angulation of said second planar member as it deviates from parallel with respect to said first planar member.

4. The dynamic spacer of claim 1, wherein said tensioning means comprises a plurality of compressive coil-type springs.

5. The dynamic spacer of claim 1, wherein said tensioning means comprises a plurality of segmental cylindrical spring housings each having an upper section and a lower section, said lower section fixedly attached to said upper tensioning surface of said first planar member and said upper section fixedly attached to said lower tensioning surface of said second planar member, each of said plurality of segmental cylindrical spring housings encapsulating a compressive coil-type spring, said upper section of said segmental cylindrical spring housing having a first diameter and said lower section of said segmental cylindrical spring housing having a second diameter smaller than said first diameter of said upper section, and said lower section of said segmental cylindrical spring housing capable of being slidingly engaged within said upper section of said segmental cylindrical spring housing.

6. The dynamic spacer of claim 5, wherein said lower section of said segmental cylindrical housing comprises graduated indicia for measuring a distance between said lower tissue engaging surface of said first planar member and said upper tissue engaging surface of said second planar member.

7. The dynamic spacer of claim 6, further comprising a means for measuring an angulation of said second planar member as it deviates from parallel with respect to said first planar member.

8. The dynamic spacer of claim 7, wherein said means for measuring the angulation of said second planar member as it deviates from parallel with respect to said first planar member comprises a positioner, said positioner fixedly attached to said lower tensioning surface of said second planar member, and a graduated gauge fixedly attached to said upper tensioning surface of said first planar member such that said positioner varies its position relative to said graduated gauge upon said second planar member's deviation form parallel with respect to said first planar member.

* * * * *